United States Patent [19]
Plass et al.

[11] Patent Number: 5,232,453
[45] Date of Patent: Aug. 3, 1993

[54] CATHETER HOLDER

[75] Inventors: Ronald A. Plass; Keith G. M. Hollands, both of Sussex, Great Britain

[73] Assignee: E. R. Squibb & Sons, Inc., Princeton, N.J.

[21] Appl. No.: 899,955

[22] Filed: Jun. 17, 1992

Related U.S. Application Data

[63] Continuation of Ser. No. 812,862, Dec. 20, 1991, abandoned, which is a continuation of Ser. No. 542,341, Jun. 22, 1990, abandoned.

[30] Foreign Application Priority Data

Jul. 14, 1989 [GB] United Kingdom ............... 8916191
Aug. 9, 1989 [GB] United Kingdom ............... 8918171

[51] Int. Cl.⁵ .............................................. A61M 5/32
[52] U.S. Cl. ............................. 604/180; 128/DIG. 26
[58] Field of Search ............... 604/174, 177, 180, 307, 604/394; 128/DIG. 26

[56] References Cited

U.S. PATENT DOCUMENTS

| | | |
|---|---|---|
| 3,339,546 | 9/1967 | Chen . |
| 3,683,911 | 8/1972 | McCormick ...................... 604/180 |
| 3,826,254 | 7/1974 | Mellor . |
| 3,834,380 | 9/1974 | Boyd . |
| 4,074,397 | 2/1978 | Rosin . |
| 4,080,970 | 3/1978 | Miller . |
| 4,096,863 | 6/1978 | Kaplan et al. . |
| 4,122,857 | 10/1978 | Haerr . |
| 4,192,785 | 3/1980 | Chen et al. . |
| 4,333,468 | 6/1982 | Geist . |
| 4,360,025 | 11/1982 | Edwards ........................ 604/180 |
| 4,378,012 | 3/1983 | Brown . |
| 4,392,857 | 8/1983 | Beran ............................. 604/179 |
| 4,393,080 | 7/1983 | Pawelchak et al. . |
| 4,397,647 | 8/1983 | Gordon .......................... 604/180 |
| 4,416,664 | 11/1983 | Womack ........................ 604/174 |
| 4,460,356 | 7/1984 | Moseley ......................... 604/180 |
| 4,484,914 | 11/1984 | Brown ............................ 604/180 |
| 4,527,559 | 7/1985 | Roxburg et al. . |
| 4,533,349 | 8/1985 | Bark ............................... 604/174 |
| 4,551,490 | 11/1985 | Doyle et al. . |
| 4,571,245 | 2/1986 | Hubbard et al. ............... 604/179 |
| 4,586,919 | 5/1986 | Taheri ............................ 604/9 |
| 4,617,017 | 10/1986 | Hubbard et al. ............... 604/179 |
| 4,645,492 | 2/1987 | Weeks ............................ 604/174 |
| 4,662,873 | 5/1987 | Lash .............................. 604/179 |
| 4,683,882 | 8/1987 | Laird . |
| 4,699,616 | 10/1987 | Nowak et al. .................. 604/180 |
| 4,711,636 | 12/1987 | Bierman ........................ 604/180 |
| 4,717,385 | 1/1988 | Cameron et al. .............. 604/174 |
| 4,762,738 | 9/1988 | Keyes et al. . |
| 4,799,923 | 1/1989 | Campbell ....................... 604/179 |
| 4,801,296 | 1/1989 | Vaillancourt ................... 604/272 |
| 4,822,342 | 4/1989 | Brawner ........................ 604/180 |
| 4,830,914 | 5/1989 | Vaillancourt . |
| 4,838,868 | 6/1989 | Forgor et al. .................. 604/180 |
| 4,874,340 | 10/1989 | Hesketh ........................ 604/180 |
| 4,915,694 | 4/1990 | Yamamoto et al. ............ 604/180 |
| 4,976,700 | 12/1990 | Tollini ............................ 604/180 |
| 5,037,397 | 8/1991 | Kalt et al. ...................... 604/180 |

FOREIGN PATENT DOCUMENTS

| | | |
|---|---|---|
| 206558 | 12/1986 | European Pat. Off. . |
| 2199499 | 7/1988 | United Kingdom . |
| 2211417 | 7/1989 | United Kingdom . |

*Primary Examiner*—John D. Yasko
*Assistant Examiner*—Ronald K. Stright
*Attorney, Agent, or Firm*—Stuart E. Krieger

[57] ABSTRACT

A catheter holder has a pad of medical grade adhesive material having one surface for attachment to the skin of a wearer, and a pair of tapes secured to and extending from the other surface of the pad. A multiple use adhesive is placed on a surface of at least one tape which surface faces generally towards the other tape. With such an arrangement, the two tapes can be stuck together to enclose the catheter and at the same time the tape carrying the adhesive sticks to the adjacent wall of the catheter so preventing logitudinal movement of the catheter relative to the pad.

3 Claims, 2 Drawing Sheets

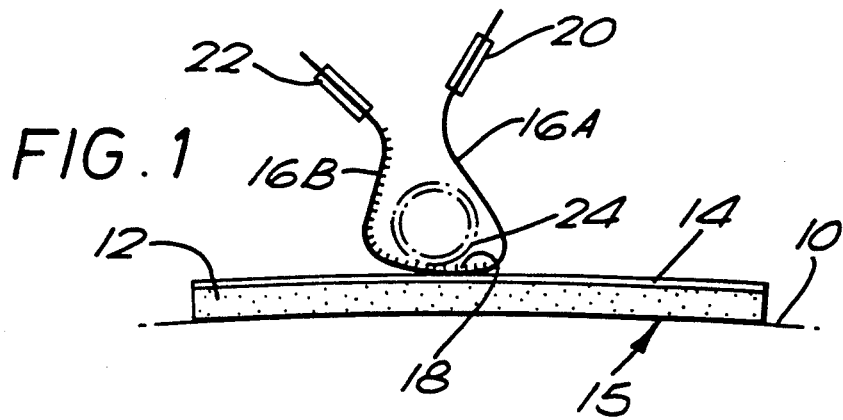
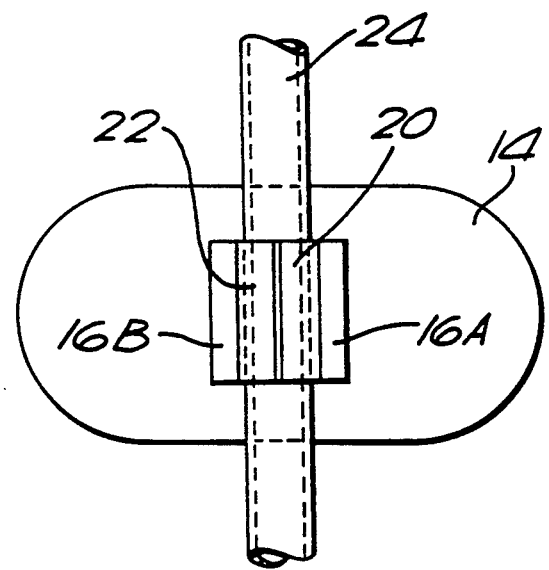

CATHETER HOLDER

This is a continuation application of application Ser. No. 07/812,862, filed Dec. 20, 1991 now abandoned which is a continuation of application Ser. No. 07/542,341, filed Jun. 22, 1990, now abandoned.

BACKGROUND OF THE INVENTION

As a result of various medical procedures, catheters often are employed to drain body fluids or administer substances. Various devices have been developed for the purpose of securing a catheter or other tubing to the body of the patient to prevent accidental dislodgement. Devices which rely on an adhesive attachment to the catheter or tubing are shown, for example, by Mellor in U.S. Pat. No. 3,826,254, Haerr in U.S. Pat. No. 4,122,857, Geist in U.S. Pat. No. 4,333,468, Brown in U.S. Pat. No. 4,484,914, Moseley in U.S. Pat. No. 4,460,356, Vaillancourt in U.S. Pat. Nos. 4,801,296 and 4,830,914, Hesketh in U.K. Patent Application 2,211,417, and Muller in European Patent Application 206,558. Other devices have been developed which secure the catheter by a means of interengageable fabric such as Velcro as shown, for example, by Boyd in U.S. Pat. No. 3,834,380, Rosin in U.S. Pat. No. 4,074,397, Kaplan et al. in U.S. Pat. No. 4,096,863, Womack in U.S. Pat. No. 4,416,664, Hubbard et al. in U.S. Pat. Nos. 4,571,245 and 4,617,017 and Campbell in U.S. Pat. No. 4,799,923. Other devices have been developed which rely on a mechanical means to secure the catheter as shown, for example, by Edwards in U.S. Pat. No. 4,360,025, Brown in U.S. Pat. No. 4,378,012, Beran in U.S. Pat. No. 4,392,857, Gordon in U.S. Pat. No. 4,397,647, Taheri in U.S. Pat. No. 4,586,919, Weeks in U.S. Pat. No. 4,645,492, Nowak et al. in U.S. Pat. No. 4,699,616, Bierman in U.S. Pat. No. 4,711,636, Cameron et al. in U.S. Pat. No. 4,717,385, and Hesketh in U.S. Pat. No. 4,874,380.

SUMMARY OF THE INVENTION

According to the invention, there is provided a catheter holder comprising a pad of medical grade adhesive material having one surface for attachment to the skin of a wearer, a pair of tapes secured to and extending from the other surface of the pad, and multiple use adhesive on a surface of at least one tape, said surface facing generally towards the other tape. With such an arrangement, the two tapes can be stuck together to enclose the catheter and at the same time the tape carrying the adhesive sticks to the adjacent wall of the catheter so preventing longitudinal movement of the catheter relative to the pad.

Optionally, the pad may have an opening or hole near the point of attachment of the tapes, so that the catheter can be threaded through the pad. Alternatively, the pad may be slit inwardly from its edge with the slit joining a hole. This arrangement enables a catheter to be engaged with the device without a threading operation. It is often necessary to avoid threading, e.g., where one end of the catheter is attached internally of the wearer and the other end is attached to a container for the discharge of exudate.

An important advantage of this invention is that the catheter holder can accomodate many different sizes of catheters. This is in marked contrast to most if not all of the catheter holders currently available. These suffer from the disadvantage that, when a larger catheter is to be used, there is the need to search for and obtain a catheter holder of a size precisely appropriate to the catheter concerned. Another advantage of an embodiment of the invention is that the catheter can be satisfactorily held and re-held after adjustment whether it extends from the body of the wearer substantially perpendicular to the skin, or at some lesser angle.

BRIEF DESCRIPTION OF THE DRAWINGS

FIG. 1 is a side elevation of a catheter holder in accordance with the invention showing tapes thereof separated;

FIG. 2 is a plan view of the catheter holder shown in FIG. 1 but showing the tapes stuck together;

DETAILED DESCRIPTION OF THE INVENTION

Figure 3:
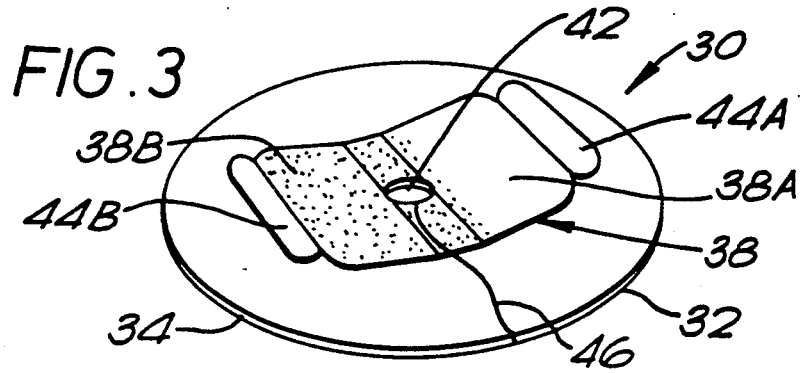
FIG. 3 illustrates a second embodiment of the invention, having a circular pad of medical grade adhesive.

The catheter holder illustrated in FIGS. 1 and 2 includes a pad of medical grade adhesive material 12. The pad 12 has on its top or free surface a film 14 of a synthetic plastics material. The pad 12 is shown as applied to the skin of a wearer, the skin being denoted by 10. Prior to application, the surface 15 of the pad 12 is covered by a strippable release paper or sheet.

Any of the known medical grade pressure sensitive adhesives can be employed. Preferably, adhesive material 12 is formulated by blending one or more water soluble or swellable hydrocolloids with a polyisobutylene or a mixture of polyisobutylenes or a mixture of one or more polyisobutylenes and one or more non-acrylic elastomers. Other materials can be included within the adhesive formulations such as mineral oil, tackifiers, antioxidants, cohesive strengthening agents, and pharmaceutically active materials such as antiinflammatory agents, antiseptics, or materials having skin healing or soothing properties. Suitable adhesive formulations are taught by Chen in U.S. Pat. No. 3,339,546, Chen et al. in U.S. Pat. No. 4,192,785, Pawelchak et al. in U.S. Pat. No. 4,393,080, Doyle et al. in U.S. Pat. No. 4,551,490, and by Keyes et al. in U.S. Pat. No. 4,762,738. As disclosed in these references, suitable water soluble and water swellable hydrocolloids include sodium carboxymethylcellulose, pectin, gelatin, guar gum, locust bean gum, gum karaya, and mixtures thereof. Suitable cohesive strengthening agents include water-insoluble cross-linked sodium carboxymethylcellulose, water-insoluble cross-linked dextran, etc. Suitable non-acrylic elastomers include butyl rubber and styrene radial or block copolymers such as styrene-butadiene-styrene (S-B-S) and styrene-isoprene-styrene (S-I-S) block type copolymers.

A pair of tape or strip members 16A, 16B are attached to the film 14 in any suitable manner. These tapes may be synthetic plastics strips. They may be formed by a single strip of material fastened to the film 14 at an intermediate region. A nonadhesive grippable tab 20 is carried by the free end of the tape 16A and a similar tab 22 is carried by the tape member 16B. Although referred to as two separate tapes, it will be understood that equally efficient results can be obtained by using a single tape member having two free ends. A multi-use adhesive 18 is applied to a length of the inner surface of the tape member 16B, covering all or most of the region where the tape is attached to the film 14 and extending up nearly to the gripping tab 22. The corresponding inner surface of the tape 16A is free of adhesive. With this arrangement, the tape 16A and 16B can be pressed together and remain stuck together but can readily be separated by pulling apart the tabs 20 and 22. The sticking together and separating operations can be successfully repeated in accordance with the characteristics of the chosen multi-use adhesive.

Multi-use refers to the ability of the adhesive to retain its tack after it is peeled from a surface so that it can be refastened. Such adhesives are commercially available, for example from the 3M Company, and are employed in various products such as adhesive tabs on diapers.

In use, a length of a catheter 24 is placed between the tape members 16A and 16B and these are then pinched together to tightly surround and enclose the catheter 24. The adhesive on the tape 16B attaches to the catheter and prevents the catheter 24 being moved in the direction of its length relative to the catheter holder, but the catheter can readily be removed by separating the tape members 16A and 16B. In addition, if desired the medical grade adhesive pad 12 can be removed from the skin 10 without releasing the catheter 24 from the catheter holder.

Although not shown in FIGS. 1 and 2, the pad 12 may have a slit therein. This is useful in the case that the catheter 24 extends into the body through a surgically made aperture, because the medical grade adhesive pad can then be slid into position by moving it relative to the catheter so that the catheter slides into the end of the slot in the pad 12. Thereafter the pad 12 is stuck to the skin 10 and the tape members are closed to securely retain the catheter as described above.

Figure 4:
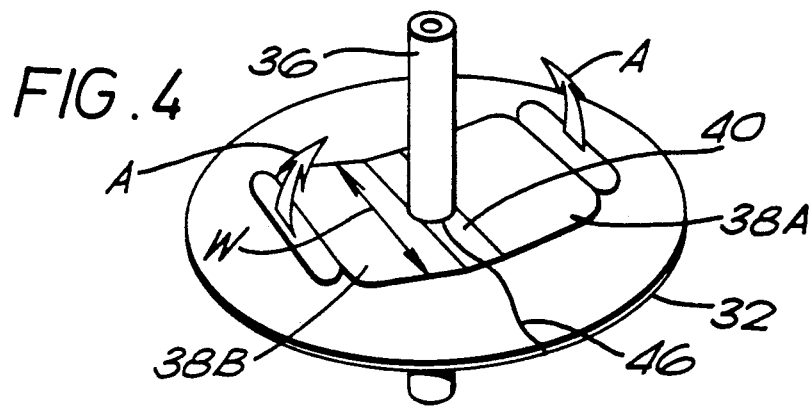
FIG. 4 is similar to FIG. 3 but shows a catheter extending through the pad and the tapes in their unjoined inoperative position.
Figure 5:
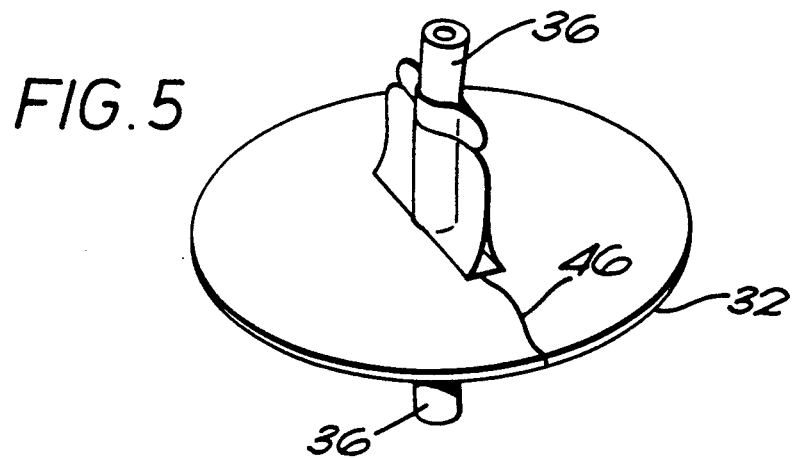
FIG. 5 is similar to FIGS. 3 and 4 but shows the two tapes stuck together to surround and grip the catheter.

Referring now to FIGS. 3-5 the illustrated catheter holder 30 includes a pad 32 of medical grade adhesive. This is shown as circular but could be oval or of any other suitable shape. The pad 32 may be made of the same materials as pad 12 referred to above. A film 34 of synthetic plastics material overlaps one surface of the pad 32. The other surface is intented for direct application to the skin of a wearer, surrounding the exit point from the body of the catheter 36. A pair of tape or strip members 38A, 38B are attached to the film 34. The tapes are preferably synthetic plastics strips. They may be formed by a single strip 38 joined to the film 34 over an intermediate region 40. The join may be by adhesive or plastics heat welding or plastics RF welding. The pad 32 has a central hole 42 and this is connected to the periphery of the pad by a curved slit 46. The slit 46 extends completely through the thickness of the pad 32, the film 34 and the tape 38. It enables a catheter to be passed through the hole 42 without either end of the catheter having to be freed or disconnected. This is an essential requirement in some circumstances where a catheter is used.

An area of the tape 38 (the area being indicated by dots in FIG. 3) is coated with a multi-use adhesive. At each end of the tape is a tab 44A, 44B, which may be colored differently from the remainder of the tape 38 or may be of a different material. Alternatively, the tab may be formed by attaching a facing to the tape 38 over the areas 44A and 44B. The tabs are non-adhesive and in use are gripped to peel apart the adhered tapes 38A, 38B. As will be seen, the bulk of the area of the tape 38A is free of adhesive; this allows the tapes 38A and 38B to be peeled apart.

In use, as indicated by the arrows A in FIG. 4, the two tapes 38A and 38B can be folded up to encase a catheter 36 which extends out of the wearer's body substantially perpendicularly to the plane of the pad 32, so holding the catheter in the desired position (FIG. 5).

Although not shown in FIGS. 1-5, the adhesive on the tapes 16A, 16B, 38A, 38B is normally covered with a strippable protective release paper or film, to avoid the adhesive picking up dirt or being degraded prior to use.

In one preferred embodiment of the holder illustrated in FIGS. 3-5, the pad has a diameter of about 80-100 mm, a thickness of about 0.8 to 2.0 mm, and the tapes are about 28 to 45 mm wide. The hole 42 may be about 7.5 mm in diameter, or such other value as may accommodate the required catheter, and the length of the tape 38 measured flat may be about 60 to 70 mm. Of this length, the tabs 44A, 44B, each occupy about 6-8 mm. These dimensions have been found satisfactory for a variety of applications, but of course the invention can be carried into effect in catheter holders which are either larger or smaller than these dimensions. In general, it is desirable that the width W (FIG. 4) of the tapes should be about 4 d to 6.5 d, preferably 5 d to 6 d, where d is the diameter of hole 42.

The catheter holder shown in FIGS. 3-5 may be integrated with or securely connected to an ostomy coupling element constructed for co-operation with a complementary coupling element on a bile bag. The pad and bag are arranged so that the free end of the catheter empties into the bag. The resulting combination can be termed a "bile kit" and provides a means whereby bile may be drained from a patient into a bag, and the bag may be removed, emptied, and replaced with a fresh bag, all without disturbing the catheter and without detaching the pad 32 from the wearer.

It will be understood that modifications may be made to the catheter holders particularly described abd illustrated herein, without departing from the invention. For example, the tape members need not be of synthetics plastics material but could be of other material which could carry a suitable multi-use adhesive. The shape and positioning of the tape members on the pad 12 or 32 need not be precisely as illustrated. In certain circumstances it may be practical to dispense with the cover film 14 or 34. Gripping tabs other than those of the kind illustrated in the Figures may be utilized. Also, the holders are useful for securing other types of tubing, wires, etc., in addition to drainage catheters, to the patient as may be required.

What is claimed is:

1. A catheter holder comprising a pad having a top surface and bottom surface, said bottom surface having an adhesive for adhesively securing said pad to the skin of a patient, said top surface having two tape portions secured thereto, each of said tape portions having a free end with non-adhesive grippable tabs, said secured tape portions being spaced apart on said top surface so as to form a longitudinal strip therebetween for accommodating a catheter extending transverse to said pad, said pad having a hole extending through said strip for accommodating a catheter extending substantially perpendicular therethrough, said pad having a slit extending from its edge to said hole to permit placement of a catheter through said slit into said hole, each of said tape portions having a surface opposing a surface of said other tape portion, at least one of said opposing surfaces having a multiple use adhesive, said tape portions being capable of gripping between said opposing surfaces either a catheter extending across said strip and transversely to said pad or perpendicularly through said hole.

2. A catheter holder according to claim 1 in which the width of the tapes is from 4 to 6.5 d where d is the diameter of the hole.

3. A catheter holder according to claim 1 in which the width of the tapes is from 5 d to 6 d.

* * * * *